United States Patent
Toledano et al.

(10) Patent No.: US 10,688,462 B2
(45) Date of Patent: Jun. 23, 2020

(54) MICROCAPSULES COMPRISING ACTIVE INGREDIENTS AND A METAL OXIDE SHELL, A METHOD FOR THEIR PREPARATION AND USES THEREOF

(75) Inventors: Ofer Toledano, Kfar Saba (IL); Hanan Sertchook, Gedera (IL); Natalia Loboda, Jerusalem (IL); Raed Abu-Reziq, Jatt Hamesholash (IL)

(73) Assignee: SOL-GEL TECHNOLOGIES LTD., Ness Ziona (IL)

( * ) Notice: Subject to any disclaimer, the term of this patent is extended or adjusted under 35 U.S.C. 154(b) by 293 days.

(21) Appl. No.: 13/056,952

(22) PCT Filed: Aug. 2, 2009

(86) PCT No.: PCT/IL2009/000751
§ 371 (c)(1),
(2), (4) Date: Apr. 6, 2011

(87) PCT Pub. No.: WO2010/013250
PCT Pub. Date: Feb. 4, 2010

(65) Prior Publication Data
US 2011/0177951 A1    Jul. 21, 2011

Related U.S. Application Data

(60) Provisional application No. 61/085,255, filed on Jul. 31, 2008.

(51) Int. Cl.
| | |
|---|---|
| *B01J 13/14* | (2006.01) |
| *A61K 8/28* | (2006.01) |
| *A61K 8/25* | (2006.01) |
| *A61K 8/27* | (2006.01) |
| *A01N 25/28* | (2006.01) |
| *A61K 8/29* | (2006.01) |
| *A61K 8/11* | (2006.01) |
| *A61Q 19/00* | (2006.01) |

(52) U.S. Cl.
CPC .............. *B01J 13/14* (2013.01); *A01N 25/28* (2013.01); *A61K 8/11* (2013.01); *A61K 8/25* (2013.01); *A61K 8/27* (2013.01); *A61K 8/28* (2013.01); *A61K 8/29* (2013.01); *A61Q 19/00* (2013.01); *A61K 2800/412* (2013.01)

(58) Field of Classification Search
CPC combination set(s) only.
See application file for complete search history.

(56) References Cited

U.S. PATENT DOCUMENTS

| | | | |
|---|---|---|---|
| 4,931,362 A | 6/1990 | Zsifkovits et al. | |
| 5,310,721 A | 5/1994 | Lo | |
| 5,500,223 A | 3/1996 | Behan et al. | |
| 6,238,650 B1 | 5/2001 | Lapidot et al. | |
| 6,251,313 B1 | 6/2001 | Deubzer et al. | |
| 6,303,149 B1 | 10/2001 | Magdassi et al. | |
| 6,337,089 B1 | 1/2002 | Yoshioka et al. | |
| 6,436,375 B1 | 8/2002 | Lapidot et al. | |
| 6,468,509 B2 | 10/2002 | Lapidot et al. | |
| 6,703,032 B2 | 3/2004 | Gers-Barlag | |
| 6,855,335 B2 | 2/2005 | Seok et al. | |
| 7,202,991 B2 | 4/2007 | Zhang | |
| 2002/0064541 A1 | 5/2002 | Lapidot | |
| 2004/0202682 A1 | 10/2004 | Emrick | |
| 2004/0234738 A1 | 11/2004 | Jahns | |
| 2005/0037087 A1 | 2/2005 | Lapidot | |
| 2005/0156340 A1 | 7/2005 | Valianatos | |
| 2005/0201955 A1 | 9/2005 | Bunger | |
| 2006/0008440 A1 | 1/2006 | Blatt | |
| 2006/0199011 A1 | 9/2006 | Jahns | |
| 2010/0203121 A1 | 8/2010 | Toledano et al. | |
| 2011/0177951 A1 | 7/2011 | Toledano et al. | |
| 2012/0202695 A1 | 8/2012 | Toledano et al. | |
| 2013/0095185 A1 | 4/2013 | Toledano et al. | |
| 2018/0101284 A1 | 4/2018 | Pope et al. | |
| 2018/0117369 A1 | 5/2018 | Toledano et al. | |
| 2018/0207451 A1 | 7/2018 | Toledano et al. | |
| 2018/0339176 A1 | 11/2018 | Toledano et al. | |

FOREIGN PATENT DOCUMENTS

| | | |
|---|---|---|
| EP | 0934773 | 8/1999 |
| EP | 0941761 A2 | 9/1999 |
| GB | 2416524 | 2/2006 |
| WO | 0009652 | 2/2000 |
| WO | 0071084 | 11/2000 |
| WO | 0072806 | 12/2000 |
| WO | 0180823 | 11/2001 |
| WO | 03003497 | 1/2002 |
| WO | 03039510 | 5/2003 |
| WO | WO-2003034979 A2 | 5/2003 |
| WO | 03066209 | 8/2003 |

(Continued)

OTHER PUBLICATIONS

International Search Report; PCT/IL2009/000751; dated May 18, 2010.
J. Giermanska-Kahn, "A New Method to Prepare Monodisperse Pickering Emulsions" Langmuir 2002, 18, 2515-2518.
R. Miller, "Composite interfacial layers containing micro-size and nano-size particles", Advances in Colloid and Interface Science 128-130 (2006) 17-26.
Shigeru Ikeda, "Direct Observation of Amphiphilic Silica Particles Assembled at an Oil-Water Interface" Chemistry Letters vol. 34, No. 10 (2005).
K. P. Velikov, "Direct Observation of the Dynamics of Latex Particles Confined inside Thinning Water-Air Films", Langmuir 1998, 14, 1148-1155.

(Continued)

*Primary Examiner* — John Pak
*Assistant Examiner* — Daniel L Branson
(74) *Attorney, Agent, or Firm* — Mark S. Cohen; Pearl Cohen Zedek Latzer Baratz LLP

(57) ABSTRACT

The present invention provides a process for preparing microcapsules comprising a core material encapsulated by a metal oxide shell, microcapsules obtained therewith and uses thereof.

13 Claims, No Drawings

(56) References Cited

FOREIGN PATENT DOCUMENTS

| WO | 2004081222 | | 9/2004 |
|---|---|---|---|
| WO | 2005009604 | | 2/2005 |
| WO | WO 2005009604 A1 * | | 2/2005 |
| WO | WO-2005009604 A1 | | 2/2005 |
| WO | 2006127172 A2 | | 11/2006 |
| WO | 2007006765 A1 | | 1/2007 |
| WO | 2007015243 | | 2/2007 |
| WO | WO 2007015243 A2 * | | 2/2007 |
| WO | 2007033931 A1 | | 3/2007 |
| WO | 2008030749 A2 | | 3/2008 |
| WO | 2008072239 | | 6/2008 |
| WO | 2008083092 A2 | | 7/2008 |
| WO | WO-2008093346 A2 | | 8/2008 |

OTHER PUBLICATIONS

Fei Yang, "Effect of dispersion pH on the formation and stability of Pickering emulsions stabilized by layered double hydroxides particles" Journal of Colloid and Interface Science 306 (2007) 285-295.
Tommy S. Horozov, "Effect of particle hydrophobicity on the formation and collapse of fumed silica particle monolayers at the oil-water interface", Colloids and Surfaces A: Physicochem. Eng. Aspects 282-283 (2006) 377-386.
Bernard P. Binks, "Effects of pH and Salt Concentration on Oil-in-Water Emulsions Stabilized Solely by Nanocomposite Microgel Particles", Langmuir 2006, 22, 2050-2057.
Krassimir D. Danov, "Electric forces induced by a charged colloid particle attached to the water-nonpolar fluid interface" Journal of Colloid and Interface Science 298 (2006) 213-231.
Mirjam E. Leunissen, "Electrostatics at the oil-water interface, stability, and order in emulsions and colloids", PNAS Feb. 20, 2007 vol. 104 No. 8 2585-2590.
Trond Erik Havre, "Emulsion stabilization by means of combined surfactant multilayer (D-phase) and asphaltene particles", Colloids and Surfaces A: Physicochem. Eng. Aspects 228 (2003) 131-142.
Navid Saleh, "Adsorbed Triblock Copolymers Deliver Reactive Iron Nanoparticles to the Oil/Water Interface", Nano Letters 2005, vol. 5, No. 12, 2489-2494.
Robert Aveyard, "Emulsions stabilised solely by colloidal particles", Advances in Colloid and Interface Science, 100-102 (2003) 503-546.
Annie Steinchen, "From dispersed nano-objects to solutions—A thermodynamic approach", Colloids and Surfaces A: Physicochem. Eng. Aspects, (2007) p. 1-4.
Qiang Lan, "Synthesis of bilayer oleic acid-coated Fe3O4 nanoparticles and their application in pH-responsive Pickering emulsions", Journal of Colloid and Interface Science 310 (2007) 260-269.
Spomenka Simovic, "Hydrophilic Silica Nanoparticles at the PDMS Droplet-Water Interface", Langmuir 2003, 19, 3785-3792.
Syuji Fujii, "Hydroxyapatite nanoparticles as stimulus-responsive particulate emulsifiers and building block for porous materials", Journal of Colloid and Interface Science (2007) p. 1-10.
Ailin Ding, "Influence of Particle Hydrophobicity on Particle-Assisted Wetting", Langmuir 2005, 21, 1371-1376.
N. Neirynck, "Influence of pH and biopolymer ratio on sodium caseinate-guar gum interactions in aqueous solutions and in O/W emulsions", Food Hydrocolloids 21 (2007) 862-869.
Jasper L. Dickson, "Interactions of Core-Shell Silica Nanoparticles in Liquid Carbon Dioxide Measured by Dynamic Light Scattering", Ind. Eng. Chem. Res. 2006, 45, 5603-5613.
Bernard P. Binks, "Inversion of Silica-Stabilized Emulsions Induced by Particle Concentration", Langmuir 2005, 21, 3296-3302.
P.M. Kruglyakov, "Investigation of the influence of capillary pressure on stability of a thin layer emulsion stabilized by solid particles", Colloids and Surfaces A: Physicochem. Eng. Aspects 263 (2005) 330-335.
Spomenka Simovic, "Adsorption of Hydrophobic Silica Nanoparticles at the PDMS Droplet-Water Interface", Langmuir 2003, 19, 8364-8370.

Daisuke Suzuki, "Janus Microgels Prepared by Surfactant-Free Pickering Emulsion-Based Modification and Their Self-Assembly" J. Am. Chem. Soc. 2007, 129, 8088-8089.
Catherine P. Whitby, "Nanoparticle adsorption and stabilisation of surfactant-free emulsions", Journal of Colloid and Interface Science 301 (2006) 342-345.
Bernard P. Binks, "Nanoparticle silica-stabilised oil-in-water emulsions: improving emulsion stability", Colloids and Surfaces A: Physicochem. Eng. Aspects 253 (2005) 105-RCP115.
Spomenka Simovic, "Nanoparticles of Varying Hydrophobicity at the Emulsion Droplet-Water Interface: Adsorption and Coalescence Stability", Langmuir 2004, 20, 8357-8365.
B. P. Binks, "Naturally Occurring Spore Particles at Planar Fluid Interfaces and in Emulsions", Langmuir 2005, 21, 8161-8167.
Ana Maria Fernandez, "New green surfactants for emulsion polymerization", Progress in Organic Coatings 53 (2005) 246-255.
To Ngai, "Novel emulsions stabilized by pH and temperature sensitive microgels", Chem. Commun., 2005, 331-333 | 331.
Yongjun He, "Novel Janus Cu2(OH)2CO3/CuS microspheres prepared via a Pickering emulsion route", Journal of Colloid and Interface Science 306 (2007) 296-299.
Danuta M. Sztukowski, "Oilfield solids and water-in-oil emulsion stability", Journal of Colloid and Interface Science 285 (2005) 821-833.
G. Kaptay, "On the equation of the maximum capillary pressure induced by solid particles to stabilize emulsions and foams and on the emulsion stability diagrams", Colloids and Surfaces A: Physicochem. Eng. Aspects 282-283 (2006) 387-401.
Toru Shiomi, "Biomimetic Synthesis of Lysozyme-Silica Hybrid Hollow Particles Using Sonochemical Treatment: Influence of pH and Lysozyme Concentration on Morphology", Toru Shiomi, American Chemical Society 2007.
P. A. Kralchevsky, "On the Thermodynamics of Particle-Stabilized Emulsions: Curvature Effects and Catastrophic Phase Inversion", Langmuir 2005, 21, 50-63.
Hui Xu, "Particle Bridging between Oil and Water Interfaces", Langmuir 2007, 23, 4837-4841.
Bernard P. Binks, "Particles as surfactants-similarities and differences", Current Opinion in Colloid & Interface Science 7 (2002) 21-41.
C. Zeng, "Particles on droplets: From fundamental physics to novel materials", Solid State Communications 139 (2006) 547-556.
Tommy S. Horozov, "Particle-Stabilized Emulsions: A Bilayer or a Bridging Monolayer?", Angew. Chem. Int. Ed. 2006, 45, 773-776.
Andreas Hannisdal, "Particle-stabilized emulsions: Effect of heavy crude oil components pre-adsorbed onto stabilizing solids", Colloids and Surfaces A: Physicochem. Eng. Aspects 276 (2006) 45-58.
Angelika Menner, "Particle-Stabilized Surfactant-Free Medium Internal Phase Emulsions as Templates for Porous Nanocomposite Materials: poly-Pickering-Foams", Langmuir 2007, 23, 2398-2403.
Fei Yang, "Pickering emulsions stabilized solely by layered double hydroxides particles: The effect of salt on emulsion formation and stability", Journal of Colloid and Interface Science 302 (2006) 159-169.
Sonia Melle, "Pickering Emulsions with Controllable Stability", Langmuir 2005, 21, 2158-2162.
Patrick J. Colver, "Cellular Polymer Monoliths Made via Pickering High Internal Phase Emulsions", Chem. Mater. 2007, 19, 1537-1539.
Peihong Ni, "Poly(dimethylamino)ethyl Methacrylate for Use as a Surfactant in the Miniemulsion Polymerization of Styrene", Langmuir 2006, 22, 6016-6023.
Yuyang Liu, "Polymer microspheres stabilized by titania nanoparticles", Materials Letters 60 (2006) 3731-3734.
D. J. Voorn, "Polymer-Clay Nanocomposite Latex Particles by Inverse Pickering Emulsion Polymerization Stabilized with Hydrophobic Montmorillonite Platelets", Macromolecules 2006, 39, 2137-2143.
Holger Strohm, "Porous TiO2 hollow spheres by liquid phase deposition on polystyrene latex-stabilised Pickering emulsions", J. Mater Chem. 2004, 14, 2667-2673.

(56) References Cited

OTHER PUBLICATIONS

B.R. Midmore, "Preparation of a novel silica-stabilized oil/water emulsion", Colloids and Surfaces A: Physicochemical and Engineering Aspects 132 (1998) 257-265.
Q.Y. Xu, "Preparation of particle-stabilized oil-in-water emulsions with the microchannel emulsification method", Colloids and Surfaces A: Physicochem. Eng. Aspects 262 (2005) 94-100.
Lenore L. Dai, "Self-Assembled Structure of Nanoparticles at a Liquid-Liquid Interface", Langmuir 2005, 21, 2641-2643.
Shashidhar Mini Guttula, "Self-Assembly of Colloidal Lattices at Pickering Emulsion Interfaces" Texas Tech University, Aug. 2007, p. 1-57.
Bernard P. Binks, "Solid Wettability from Surface Energy Components: Relevance to Pickering Emulsions", Langmuir 2002, 18, 1270-1273.
Teofil Jesionowski, "Characterization of silicas precipitated from solution of sodium metasilicate and hydrochloric acid in emulsion medium", Powder Technology 127 (2002) 56-65.
Claudie Bonnet, "Stabilization of Caseinate-Covered Oil Droplets during Acidification with High Methoxyl Pectin", J. Agric. Food Chem. 2005, 53, 8600-8606.
Urs T. Gonzenbach,"Stabilization of Foams with Inorganic Colloidal Particles", Langmuir 2006, 22, 10983-10988.
Loredana S. Dorobantu, "Stabilization of Oil-Water Emulsions by Hydrophobic Bacteria" Applied and Environmental Microbiology, Oct. 2004, p. 6333-6336.
Lesley E. Russell, "Stable Aqueous Nanoparticle Film Assemblies with Covalent and Charged Polymer Linking Networks", American Chemical Society 2007, p. 1-6.
M. Z. Yates, "Steric Stabilization of Colloids by Poly(dimethylsiloxane) in Carbon Dioxide: Effect of Cosolvents", Journal of Colloid and Interface Science 227, 176-184 (2000).
Stephen M. Sirard, "Steric Stabilization of Silica Colloids in Supercritical Carbon Dioxide", Ind. Eng. Chem. Res. 2004, 43, 525-534.
Tommy S. Horozov, "Structure and Stability of Silica Particle Monolayers at Horizontal and Vertical Octane-Water Interfaces", Langmuir 2005, 21, 7405-7412.
Sowmitri Tarimala, "Structure of Microparticles in Solid-Stabilized Emulsions", Langmuir 2004, 20, 3492-3494.
Agnieszka Ewa Wiacek, "Studies of oil-in-water emulsion stability in the presence of new dicephalic saccharide-derived surfactants", Colloids and Surfaces B: Biointerfaces 25 (2002) 243-256.
L. E. Helseth, "Colloidal Rings in a Liquid Mixture", Langmuir 2005, 21, 7271-7275.
Clive A. Prestidge, "Nanoparticle encapsulation of emulsion droplets", International Journal of Pharmaceutics 324 (2006) 92-100.
Sheng-Wen Zhang, "Synthesis of Silanol-Functionalized Latex Nanoparticles through Miniemulsion Copolymerization of Styrene and y-Methacryloxypropyltrimethoxysilane" Langmuir 2006, 22, 4674-4679.
Chul Oh,"Synthesis of silica microspheroids for templates in W/O reverse emulsion", Colloids and Surfaces A: Physicochem. Eng. Aspects 269 (2005) 112-118.
Cristina Alava, "Temperature-responsive emulsions: The effect of added surfactant" Colloids and Surfaces A: Physicochem. Eng. Aspects 270-271 (2005) 18-25.
Andrew P. Sullivan, "The Effects of Inorganic Solid Particles on Water and Crude Oil Emulsion Stability" Ind. Eng. Chem. Res. 2002, 41, 3389-3404.
V. Khrenov, "The formation of hydrophobic inorganic nanoparticles in the presence of amphiphilic copolymers", Colloid Polym Sci (2006) 284: 927-934.
Yuan Le, "Theoretical and experimental studies on the silica hollow spheres", Journal of Non-Crystalline Solids 353 (2007) 164-169.
S. Sacanna, "Thermodynamically Stable Pickering Emulsions", Physical Review Letters 98, 158301 (2007).
Urs T. Gonzenbach, "Ultrastable Particle-Stabilized Foams", Angew. Chem. Int. Ed. 2006, 45, 3526-3530.
Stefan A. F. Bon, "Pickering Stabilization as a Tool in the Fabrication of Complex Nanopatterned Silica Microcapsules", Langmuir 2007, 23, 9527-9530.
Vinothan N. Manoharan, "Colloidal spheres confined by liquid droplets: Geometry, physics, and physical chemistry", Solid State Communications 139 (2006) 557-561.
Shu-Ling Shen, "A novel process to synthesize magnetic hollow silica microspheres", Colloids and Surfaces A: Physicochem. Eng. Aspects, 2007 (XP022326446) p. 1-7.
P S Clegg, "Colloid-stabilized emulsions: behaviour as the interfacial tension is reduced", J. Phys.: Condens. Matter 17 (2005) S3433-S3438.
S. E. Sheppard, "Emulsification by Adsorption at an Oil-Water Interface", pp. 634-639, J. Phys. Chem. 23, (1919).
J. Mitchell Fain, "Surface Activity of Solid Emulsifiers", Industrial and Engineering Chemistry , vol. 31, No. 1, p. 48-51, Ind. Eng. Chem. 31(1), (1939).
Kim et al.; "Effect of aqueous phase composition on the stability of a silica-stabilized water-in-oil emulsion"; Jan. 2004; pp. 350-343.
"Pastes"; U.S. Pharmacopeia; 2015; 1 page.
Bon et al.; "Pickering Stabilization as a Tool in the Fabrication of Complex Nanopatterned Silica Microcapsules"; Langmuir, vol. 23; 2007; pp. 9527-9530.
Jenning et al.; "Comparison of Wax and Glyceride Solid Lipid Nanoparticles"; International Journal of Pharmaceutics, vol. 196; 2000; pp. 219-222.
Jenning et al.; "Encapsulation of Retinoids in Solid Lipid Nanoparticles (SLN)"; Journal of Microencapsulation, vol. 18, No. 2; 2001; pp. 149-158.
Prestidge et al.; "Nanoparticle Encapsulation of Emulsion Droplets"; International Journal of Pharmaceutics, vol. 324; 2006; pp. 92-100.
Date, A. A., Naik, B., & Nagarsenker, M. S. (2006). Novel drug delivery systems: potential in improving topical delivery of antiacne agents. Skin Pharmacology and Physiology, 19(1), 2-16.
Fat and why it matters—"The kinds of fats and why it matters to you", Indiana University, Copyright 2019. Retrieved online at: http://www.indiana.edu/~oso/Fat/Definitions.html.

* cited by examiner

MICROCAPSULES COMPRISING ACTIVE INGREDIENTS AND A METAL OXIDE SHELL, A METHOD FOR THEIR PREPARATION AND USES THEREOF

CROSS-REFERENCE TO RELATED APPLICATIONS

This application is a National Phase Application of PCT International Application No. PCT/IL2009/000751, International Filing Date 2 Aug, 2009, claiming priority from U.S. Provisional Application No. 61/085,255, filed 31 Jul., 2008, which is hereby incorporated by reference.

FIELD OF THE INVENTION

The present invention generally relates to process for preparing microcapsules, compositions comprising microcapsules and uses thereof.

BACKGROUND OF THE INVENTION

The following publications are considered pertinent for describing the state of the art in the field of the invention.
  U.S. Pat. No. 5,500,223
  U.S. Pat. No. 6,303,149
  U.S. Pat. No. 6,238,650
  U.S. Pat. No. 6,468,509
  U.S. Pat. No. 6,436,375
  U.S. Pat. No. 6,337,089
  US 2005037087
  US 2002064541
  U.S. Pat. No. 6,251,313
  U.S. Pat. No. 4,931,362
  U.S. Pat. No. 6,855,335
  WO 00/09652
  WO 00/72806
  WO 01/80823
  WO 03/03497
  WO 03/039510
  WO 00/71084
  WO 05/009604
  WO 04/81222
  WO 03/066209
  GB 2416524
  EP 0 934 773
  EP 0 941 761
  S. A. F. Bon et al., Pickering Stabilization as a Tool in the Fabrication of Complex Nanopatterned Silica Microcapsules, *Langmir*, 23: 9527-9530, 2007.
  C. A. Prestidge et al. Nanoparticle encapsulation of emulsion droplets, International Journal of Pharmaceutics 324:92-100, 2006.

SUMMARY OF THE INVENTION

The present invention relates to a process for preparing microcapsules comprising a core material encapsulated by a metal oxide shell, said process comprising:
  (a) preparing an oil-in-water emulsion by emulsification of an oily phase that comprises a core material, in an aqueous phase, wherein one or both of the oily phase, and the aqueous phase comprises a sol-gel precursor;
  (b) including metal oxide nanoparticles in said aqueous phase either prior, during or after (a); and
  (c) applying conditions to obtain microcapsules.

The invention further relates to microcapsules obtainable by the process as described in the present invention.

The invention additionally relates to microcapsules comprising a core material encapsulated by a metal oxide shell, wherein said core material is (i) a liquid or (ii) a dispersion in liquid; wherein the thickness of said shell is in the range 0.1-10 micron; and wherein said shell is obtained from (a) metal oxide nanoparticles, and (b) a hydrolyzed and polymerized sol gel precursor.

Moreover, the invention relates to a composition comprising microcapsules as described in the present invention; and a carrier.

The invention additionally relates to a method for treating a surface condition in a subject, comprising topically administering onto the surface a composition as described in the invention, wherein the core material comprises a topically acting active agent.

The invention further relates to a composition comprising microcapsules as described in the present invention, wherein the core material comprises a topically acting active agent, for treatment of a disease or disorder selected from acne, infection, inflammation, pruritis, psoriasis, seborrhea, contact dermatitis, rosacea, and a combination thereof.

Moreover, the invention relates to use of microcapsules as described in the present invention, wherein the core material comprises a topically acting active agent for the preparation of a medicament for topical administration on the skin or mucosal membrane.

Additionally, the invention relates to compositions for pest control comprising microcapsules as described in the present invention, wherein said core material comprises a pesticide.

DETAILED DESCRIPTION OF THE INVENTION

The present invention is based on the finding of a manner of obtaining a thick and dense coating on a liquid water insoluble core or a dispersion in a liquid water insoluble core, using metal oxide nanoparticles in combination with a sol-gel precursor.

Thus, in one aspect of the present invention, there is provided a process for preparing microcapsules comprising a core material encapsulated by a metal oxide shell, said process comprising:
  (a) preparing an oil-in-water emulsion by emulsification of an oily phase that comprises a core material, in an aqueous phase, wherein one or both of the oily phase, and the aqueous phase comprises a sol-gel precursor;
  (b) including metal oxide nanoparticles in said aqueous phase either prior, during or after (a); and
  (c) applying conditions to obtain microcapsules.

In the present invention the term "core material" refers to the inside part of the microcapsules comprising an active ingredient that is surrounded by the metal oxide shell of the microcapsules. This term refers to any material present in the core, both the active ingredient and the excipients such as the liquid carrier.

The core material which may be a water insoluble liquid or a dispersion in water-insoluble liquid comprises an active ingredient (e.g. a pesticide, dermatological active ingredient). The core material may be constituted by a water-insoluble liquid active ingredient; may comprise a first water-insoluble liquid active ingredient dissolved and/or dispersed in a second water insoluble liquid being another active ingredient or serving as a carrier medium; may comprise a solid active ingredient dissolved and/or dispersed in a water-insoluble liquid being another active ingredient or serving as a carrier medium. The active ingredient may be a single type of active ingredient or may be a combination of two or more active ingredients.

The term "water insoluble liquid" or "dispersion in water-insoluble liquid" refers to a solubility of the liquid (including the ingredients included therein, dissolved and/or dispersed) in water of about less than 1% w/w at room temperature (20-25° C.). In one embodiment a solubility of the liquid (including the ingredients included therein, dissolved and/or dispersed) in water of about 0.5% w/w at room temperature (20-25° C.). In another embodiment a solubility of the liquid (including the ingredients included therein, dissolved and/or dispersed) in water of about less than 1% w/w at room temperature (20-25° C.). In one embodiment a solubility of the liquid (including the ingredients included therein, dissolved and/or dispersed) in water of about 0.15 w/w at room temperature (20-25° C.).

Accordingly, the constituents included in the core material whether solid or liquid ingredients have a solubility of about less than 1% w/w at room temperature (20-25° C.). In one embodiment the constituents included in the core material whether solid or liquid ingredients have a solubility of about 0.5% w/w at room temperature (20-25° C.). In another embodiment, the constituents included in the core material whether solid or liquid ingredients have a solubility of about 0.15% w/w at room temperature (20-25° C.).

A water insoluble liquid may be selected from the following non-limiting list: squalane oil, polydimethylsiloxane, mineral oil, castor oil, aromatic 200, and mixtures thereof.

In the present invention, the term "sol-gel precursor" refers to any metal or semi-metal organo-metallic monomer, or a prepolymer (which means several monomers polymerized together) thereof, which allows to obtain a glass or ceramic material by in-situ polymerization (an inorganic sol-gel polymerization process). In one embodiment a sol-gel precursor is a metal or semi-metal organo-metallic monomer (e.g. a metal or semi-metal alkoxide monomer.

In the present invention, the term "active ingredient" refers to any molecule or substance that can be used in medicine, cosmetics, agriculture and which grants the final product (cosmetics, pesticide, drug, etc.) at least one desired property.

As used herein the term "metal oxide nanoparticles" refers to substantially pure metal oxide nanoparticles consisting essentially of or comprised wholly of metal oxide. In one embodiment a metal oxide nanoparticles do not include organic material, in particular not polystyrene.

According to an embodiment of the present invention said core material comprises a pharmaceutically, cosmetically, or agrochemically active ingredient.

Additionally according to another embodiment of the present invention said core material comprises a dermatologically active agent.

Further according to another embodiment of the present invention said dermatologically active agent is selected from antifungal agents, antibacterial agents, anti-inflammattory agents, antipruritic agents, anti psoriatic agent, anti acne agents, anti rosacea agents, and combinations of any of the above.

In one embodiment, said anti acne agent is selected from benzoyl peroxide, a retinoid, and mixtures thereof.

The retinoid may be for example tretinoin (all trans retinoic acid), tazarotene, iso-tretinoin, adapalene or mixtures thereof.

According to another embodiment of the present invention said agrochemical active ingredient is a pesticide.

Pesticides which may be employed in the practice of this invention include a wide range of herbicides, nematocides, insecticides, acaricides, fungicides, plant growth promoting or controlling chemicals and other crop treating products which may be solid or liquid at ambient temperatures. One of ordinary skill in the art can find a listing of suitable pesticides by consulting references such as the Ashgate Handbook of Pesticides and Agricultural Chemicals, G. W. A. Milne (ed.), Wiley Publishers (2000). Combinations of two or more pesticides may also be employed.

The pesticide may be selected from herbicides, insecticides, fungicides, and mixtures thereof.

Non limiting examples of herbicides are triazines, dinitroanilines, phenoxy esters, benzamides, chloroacetamides, isoxazolidinone, pyridine carboxamides, quinolinecarboxylates, thiocarbamates, triazolinones, triazolopyrimidines, triketones, ureas, and mixtures thereof.

Non limiting examples of insecticides are mectins, benzoyl ureas, carbamates, diacylhydrazines, isoxazoles, neonicitonoids, organophosphates, oxadiazines, phenylpyrazoles, pyrethroids, semicarbazones, strobilurons, tetronic acids, and mixtures thereof.

Non limiting examples of fungicides are benzimidazoles, carboxamides, azoles, mandelamide, morpholine, phenyl amides, and mixtures thereof.

The agrochemical active ingredient may also be pheromones, synergists, plant growth regulators.

Non limiting examples of pesticide active ingredients are: 2,4-D-2-ethylhexyl, abamectin, acetochlor, aclonifen, alachlor, aldrin, alpha-cypermethrin, ametryn, atrazine, azadirachtin, azinphos-ethyl, azinphos-methyl, azoxystrobin, benalaxyl, benalaxyl-M, bendiocarb, benfluralin, benomyl, bentazone, beta-cyfluthrin, beta-cypermethrin, bifenthrin, binapacryl, bioresmethrin, boscalid, bromophos, bromophos-ethyl, bromoxynil, butachlor, butylate, cadusafos, captafol, captan, carbaryl, carbendazim, carbofuran, carbosulfan, carboxin, carfentrazone-ethyl, chlorfenvinphos, chlorfluazuron, chlorothalonil, chlorphoxim, chlorpyrifos, chromafenozide, clodinafop-propargyl, clomazone, cloquintocet-mexyl, cloransulam-methyl, clothianidin, cyanazine, cyazofamid, cyfluthrin, cyhalofop-butyl, cyhalothrin, cypermethrin, cyproconazole, deltamethrin, diazinon, diclofop-methyl, diclofop-P-methyl, dimethomorph, dimethylvinphos, dimoxystrobin, disulfoton, dithianon, dithiopyr, diuron, dodemorph acetate, dodemorph, emamectin benzoate, endosulfan, epoxiconazole, esfenvalerate, etaconazole, ethalfluralin, ethofurnesate, etofenprox, fenamiphos, fenbuconazole, fenoxaprop-ethyl, fenpropimorph, fenvalerate, fipronil, fluazifop-butyl, fluazifop-P-butyl, fluazinam, flucythrinate, flufenacet, flufenoxuron, flumetsulam, fluotrimazole, fluoxastrobin, fluquinconazole, flusilazole, flutolanil, flutriafol, fluvalinate, folpet, fomesafen, fosmethilan, gamma-cyhalothrin, halofenozide, haloxyfop-P-methyl, hexaconazole, hydramethylnon, imidacloprid, indoxacarb, ioxynil octanoate, ipconazole, isazofos, isofenphos, isoproturon, isoxaflutole, isoxathion, karbutilate, kresoxim-methyl, lactofen, lambda-cyhalothrin, linuron, lufenuron, malathion, mancozeb, mandipropamid, MCPA-2-ethylhexyl, metaflumizone, metazachlor, metconazole, methoxyfenozide, metofluthrin, metominostrobin, metoxuron, metrafenone, metribuzin, milbemectin, myclobutanil, napropamide, nicosulfuron, nitralin, nitrofen, norflurazon, novaluron, oryzalin, oxyfluorfen, paclobutrazol, penconazole, pencycuron, pendimethalin, permethrin, petroleum oils, phenthoate, phorate, phosalone, phosdiphen, phosmet, phoxim, picloram, picolinafen, picoxystrobin, pinoxaden, piperonyl butoxide, pirimiphos-ethyl, pirimiphos-methyl, prallethrin, prochloraz, prodiamine, prometryn, propachlor, propanil, propaphos, propargite, propiconazole, pymetrozine, pyraclostrobin, pyrazophos, pyrethrins (chrysanthemates), pyridalyl, pyridate, quinclorac, quinmerac, quizalofop-ethyl, quizalofop-P-ethyl, quizalofop-P-tefuryl, resmethrin, simazine, simeconazole, S-metolachlor, spinosad, spirodiclofen, spiromesifen, spiroxamine, sulcotrione, sulfentrazone, sulprofos, tau-fluvalinate, tebuconazole, tebufenozide, tebufenpyrad, tebupirimfos, teflubenzuron, tefluthrin, temephos, terallethrin, terbacil, terbufos, tetraconazole, tetramethrin, thiacloprid, thidiazuron, thiram, tralomethrin, transfluthrin, tri-allate, triazamate, trifloxystrobin, trifluralin, triticonazole, zeta-cypermethrin, ziram, zoxamide, pheromones, sulfur, and mixtures of any of the above.

According to an embodiment of the present invention said metal oxide is selected from Silica, Titania, Zirconia, ZnO, and mixtures thereof.

According to one embodiment of the present invention said metal oxide nanoparticles have a particle size diameter (d50) in the range of 1-100 nanometer. In another embodiment, said metal oxide nanoparticles have a particle size diameter (d50) in the range of 1-50 nm. In yet a further embodiment, said metal oxide nanoparticles have a particle size diameter (d50) in the range of 5-30 nm.

By the term "particle size diameter (d50) in the range of 1-100 nanometer" is meant that 50% by volume of the particles may be less than or equal to a value in the range of 1-100 nanometer.

Unless otherwise indicated referring to size of particles will be through their $D_{90}$ meaning that 90% of the particles have the stated dimension or less (measured by volume). Thus, for examples, for nanoparticles stated to have a diameter of 10 nanometer, this means that the nanoparticles have a $D_{90}$ of 10 nanometer. The $D_{90}$ may be measured by laser diffraction.

According to one embodiment of the present invention the weight ratio of said metal oxide nanoparticles to said core material is in the range of 1:99 to 3:2. In one embodiment the weight ratio of said metal oxide nanoparticles to said core material is in the range of 1:50 to 1:1. In another embodiment the weight ratio of said metal oxide nanoparticles to said core material is in the range of 1:20 to 1:5.

According to one embodiment of the present invention the mole ratio between the metal oxide produced from said sol-gel precursor and said metal oxide nanoparticles is in the range 1:99 to 1:1. In one embodiment the mole ratio between the metal oxide produced from said sol-gel precursor and said metal oxide nanoparticles is in the range 1:50 to 1:2. In another embodiment the mole ratio between the metal oxide produced from said sol-gel precursor and said metal oxide nanoparticles is in the range 1:25 to 1:4.

According to an embodiment the process of the present invention further comprising adding a salt of a metal oxide to said aqueous phase either prior, during or after (a).

In one embodiment, said salt of metal oxide is selected from sodium silicate, potassium silicate, sodium titanate, potassium titanate, sodium zirconate, potassium zirconate, and mixtures thereof.

In one embodiment, the weight ratio of said metal oxide nanoparticles to said metal oxide salt is in the range 99:1 to 1:2. In another embodiment the weight ratio of said metal oxide nanoparticles to said metal oxide salt is in the range of 50:1 to 2:1. In a further embodiment the weight ratio of said metal oxide nanoparticles to said metal oxide salt is in the range of 50:1 to 10:1.

According to an embodiment the process of the present invention further comprising adding a binding or cross-linking additive selected from a polymeric agent, a di- or trivalent metal salt, a polyelectrolyte, and mixtures thereof, to said aqueous phase either prior, during or after (a).

In one embodiment, said polymeric agent is selected from sodium alginate, polyvinyl alcohol, carboxymethyl cellulose, polyvinyl pyrrolidone, and mixtures thereof.

In another embodiment, said di- or trivalent metal salt is selected from aluminum sulfate, sodium aluminate, sodium borate, calcium chloride, and mixtures thereof.

The purpose of using the following ingredients was to make capsules more cross-linked and strengthen the shell.

Without being bound to theory the ingredients below may act as follows:

Aluminum sulfate—the positively charged aluminum cations may be attracted to the negatively charged metal oxide nanoparticles and as such may work as cross-linkers between the metal oxide nanoparticles which are adsorbed on the oil droplet-water interface.

Sodium aluminate—sodium aluminate may react with the silanol groups on the metal oxide nanoparticles surface, and as such may work as cross-linkers between the metal oxide nanoparticles which are adsorbed on the oil droplet-water interface.

PVA (polyvinyl alcohol) may adsorb onto the metal oxide shell via hydrogen bonds and also can be cross-linked by sodium borate.

Sodium borate—sodium borate may cross link the PVA with the metal oxide shell of the microcapsules.

Sodium alginate—sodium alginate may adsorb onto the metal oxide shell (produced from adsorption of metal oxide nanoparticles) and may be cross-linked by addition of calcium chloride.

PDAC 7 (polyquaternium 7)—PDAC 7 may be used for coating of the metal oxide shell. PDAC 7 which is positively charged may adsorb onto the negatively charged metal oxide shell and as such decrease the "gaps" between the metal oxide nanopartices and thus strengthen the shell.

CMC (carboxymethyl cellulose)—CMC may be used for additional coating of the metal oxide shell. It can be used after coatings with PDAC 7.

PDAC 7 and CMC when used in combination may be added for coating and strengthening the metal oxide shell.

In one embodiment, said polyelectrolyte is selected from Polyquaternium-7 (Dimethyldiallylammonium chloride acrylamide copolymer), Polyquaternium-1 [Poly[(dimethyliminio)-2-butene-1,4-diylchloride],α[4-[tris(2-hydroxyethyl)ammonio]-2-butenyl]-ω-[tris(2-hydroxyethyl)ammonio]-, dichloride], Polyquaternium-10 [Cellulose 2-hydroxyethyl 2-(2-hydroxy-3-(trimethylammonio)propoxy)ethyl-2-hydroxy-3-(trimethylammonio)propyl ether, chloride], Chitosan, Polylysine, and mixtures thereof.

According to an embodiment of the present invention said oily phase comprises a sol-gel precursor.

According to an embodiment of the present invention said sol-gel precursors are selected from metal alkoxide monomers, semi-metal alkoxide monomers, metal ester monomers, semi-metal ester monomers and from monomers of the formula $M(R)_{-n}(P)_{-m}$, wherein M is a metallic or semi metallic element, R is a hydrolysable substituent, n is an integer from 2 to 6, P is a non polymerizable substituent and m is and integer from 0 to 6, a partially hydrolyzed and partially condensed polymer of any of the above, and mixtures of any of the above.

In one embodiment, said metallic or semi metallic element is selected from Si, Ti, Zr, Al, and Zn.

In another embodiment, said sol-gel precursors are selected from silicon alkoxide monomers, silicon ester monomers, monomers of the formula $Si(R)_n(P)_m$, where R is a hydrolysable substituent, n is an integer from 2 to 4, P is a non polymerizable substituent and m is and integer from 0 to 4, a partially hydrolyzed and partially condensed polymer of any of the above, and mixtures of any of the above.

In a further embodiment, said silicon alkoxide monomer is selected from tetramethoxy silane, tetraethoxy silane, and mixtures thereof.

In yet a further embodiment, said monomers of the formula $Si(R)_n(P)_m$ are selected from methyl trimethoxysilane, dimethyl dimethoxysilane, and mixtures thereof.

In one embodiment, the sol-gel precursor is a monomer (e.g. a metal alkoxide monomer, a semi-metal alkoxide monomer) as described hereinbefore. In one embodiment the sol-gel precursor is not a polymerized monomer, which can undergo a sol-gel process.

According to an embodiment of the present invention the pH of said aqueous phase is in the range 2-9. In one embodiment, the pH of said aqueous phase is in the range 2-7. In a further embodiment, the pH of said aqueous phase is in the range 3-5.

According to an embodiment of the present invention said conditions comprising isolating the microcapsules through procedures selected from at least one of: separation by centrifuge, filtration, evaporation, re-suspension in aqueous medium, and dialysis.

According to an embodiment of the present invention said conditions comprising pH in the range 2-9. In a further embodiment the pH is in the range 3-5.

According to one embodiment of the present invention said conditions comprising stirring.

The stirring may be for example by mechanical stirrer at 200-500 rpm.

According to another embodiment of the present invention said conditions comprising drying the obtained microcapsules in suspension.

According to one embodiment the product obtained in the process of the present invention is a suspension of said microcapsules.

According to another embodiment of the present invention the product obtained in the process of the present invention is a powder of said microcapsules.

In another aspect of the present invention there is provided microcapsules obtainable by the process of the present invention.

Yet in another aspect of the present invention there is provided microcapsules comprising a core material encapsulated by a metal oxide shell, wherein said core material is (i) a liquid or (ii) a dispersion in liquid; wherein the thickness of said metal oxide shell is in the range 0.1-10 micron; and wherein said shell is obtained from (a) metal oxide nanoparticles, and (b) a hydrolyzed and polymerized sol gel precursor.

Further according to another embodiment of the present invention the metal oxide shell has a width (thickness) of about 0.1, 0.2, 0.3, 0.4, 0.5, 0.6, 0.7, 0.8, 1, 1.5, 2 or 5 micron or above. In one embodiment the metal oxide shell has a width (thickness) of about up to 10 micron.

The core material, shell, etc. constituents may be as described in the present invention.

It is appreciated that the final form of the dispersion in a liquid may be liquid or semisolid depending on the ratio between the solid ingredients and the liquid ingredients.

The width of the metal oxide layer may be determined for example by a Transmission Electron Microscope or Confocal Microscope such that in a circular cross sectional area of the microcapsules the smallest width is at least e.g. 0.1 micron (the width is determined as the smallest distance from the outer surface of the microcapsules (i.e. metal oxide surface) to the core-metal oxide interface).

The mole ratio between the metal oxide produced from said sol-gel precursor and said metal oxide nanoparticles is in the range 1:99 to 1:1. In one embodiment mole ratio between the metal oxide produced from said sol-gel precursor and said metal oxide nanoparticles is in the range 1:50 to 1:2. In a further embodiment mole ratio between the metal oxide produced from said sol-gel precursor and said metal oxide nanoparticles is in the range 1:25 to 1:4.

According to another embodiment of the present invention said core material comprises a pharmaceutically, cosmetically, or agrochemically active ingredient.

Additionally according to one embodiment of the present invention said core material comprises a dermatologically active agent.

In one embodiment, said dermatologically active agent is selected from antifungal agents, antibacterial agents, antiinflammatory agents, antipruritic agents, anti psoriatic agent, anti acne agents, anti rosacea agents, and combinations of any of the above.

In another embodiment, said anti acne agent is selected from benzoyl peroxide, retinoid, and mixtures thereof.

In another aspect of the present invention there is provided a composition comprising a carrier and the microcapsules of the present invention.

Further in another aspect of the present invention there is provided a method for treating a surface condition in a subject, comprising topically administering onto the surface a composition of the present invention, wherein the core material comprises a topically acting active agent.

The term "treating" or "treatment" as used herein includes any treatment of a condition (disease or disorder) associated with a patient's body surface such as the skin or mucosal membrane, and includes inhibiting the disease or disorder (i.e. arresting its development), relieving the disease or disorder (i.e. causing regression of the disease or disorder), or relieving the conditions caused by the disease (i.e. symptoms of the disease). The concentrations of the dermatological agents that can be used for treatment of a specific disease or disorder may be as described in The Merck index an encyclopedia of chemical drugs, and biologicals, Rahway, N.J.; Merck & Co; 1989., incorporated herein by reference in its entirety.

Although individual needs may vary, determination of optimal ranges for effective amounts of the compositions is within the skill of the art. Generally, the dosage required to provide an effective amount of a pharmaceutical composition, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s).

According to an embodiment of the present invention said surface is skin or mucosal membrane.

According to another embodiment of the present invention said surface condition is a skin disease or disorder selected from acne, infection, inflammation, pruritis, psoriasis, seborrhea, contact dermatitis, rosacea, and a combination thereof.

Additionally, in another aspect of the present invention there is provided a composition comprising microcapsules as described in the present invention, wherein the core material comprises a topically acting active agent, for treatment of a disease or disorder selected from acne, infection, inflammation, pruritis, psoriasis, seborrhea, contact dermatitis, rosacea, and a combination thereof.

Yet, in another aspect there is provided a use of the microcapsules of the present invention, wherein said core material comprises a topically acting active agent for the preparation of a medicament for topical administration on the skin or mucosal membrane.

According to another embodiment of the invention said topical administration is for treating a disease or disorder selected from acne, psoriasis, seborrhea, contact dermatitis, infection, rosacea, inflammation, and a combination thereof.

In another aspect of the present invention there is provided a composition for pest control comprising the microcapsules of the invention, wherein said core material comprises a pesticide.

According to another embodiment of the present invention said composition is for use in crop protection or non-crop pest control.

Further according to an embodiment of the present invention said pesticide is selected from a herbicide, an insecticide, a fungicide, and mixtures thereof.

Pesticide Compositions and Uses
Composition

In one aspect, the present invention is directed to pesticidal compositions comprising the coated pesticides described above. Typically, such compositions are comprised of the coated pesticide and an agriculturally acceptable carrier. Such carriers are well known in the art and may be solids or liquids.

Other Components

To the extent that the compositions contain other components, these components make up minor portions of the composition. Minor components may also include free pesticide, which has not been incorporated into the coated pesticide (microcapsules). In addition to the other components listed herein, compositions of this invention may also contain carriers, such as for example water or other solvents in amounts equal to or greater than the major components.

The coated pesticides of this invention may be formulated and/or applied with one or more second compounds. Such combinations may provide certain advantages, such as, without limitation, exhibiting synergistic effects for greater control of pests, reducing rates of application of pesticide thereby minimizing any impact to the environment and to worker safety, controlling a broader spectrum of pests, resistance of crop plants to phytotoxicity, and improving tolerance by non-pest species, such as mammals and fish.

Second compounds include, without limitation, other pesticides, fertilizers, soil conditioners, or other agricultural chemicals. The compositions of the present invention may also contain additional surface active compounds as dispersants. Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 20% weight of the composition.

One skilled in the art will, of course, recognize that the formulation and mode of application of a pesticide may affect the activity of the material in a given application. Thus, for agricultural use, the present coated pesticides may be formulated as a granular of relatively large particle size (for example, $3/16$ or $4/8$ US Mesh), (e.g. agglomerates of coated pesticide that may redisperse in water to the primary coated pesticide), as water-dispersible granules, as powdery dusts, as wettable powders, as suspension concentrates, as capsule suspension (coated pesticide, in suspension), or as any other known types of agriculturally-useful formulations, depending on the desired mode of application. They may be applied in the dry state (e.g., as granules, powders, or tablets) or they may be formulated as concentrates (e.g., solid, liquid, gel) that may be diluted to form stable dispersions (suspensions).

Concentrates

The compositions may be formulated as concentrates by techniques known to one of ordinary skill in the art. If the composition is to be formulated as a solid, a filler such as Attaclay may be added to improve the rigidity of the granule.

The coated pesticides and pesticidal formulations may be stored and handled as solids which are dispersible into stable aqueous emulsions or dispersions prior to application. The dispersions allow uniform application from water. This is particularly advantageous at the field point of use, where normal admixing in water is all that is required before application.

The compositions of the present invention may also be in the form of wettable powders. Wettable powders are finely divided particles that disperse readily in water or other dispersant. The wettable powder is ultimately applied to the locus where pest control is needed either as a dry dust or as a dispersion in water or other liquid. Typical carriers for wettable powders include Fuller's earth, kaolin clays, silicas, and other highly absorbent, readily wet inorganic diluents. Wettable powders normally are prepared to contain about 5-80% of pesticide, depending on the absorbency of the carrier, and usually also contain a small amount of a wetting, dispersing or emulsifying agent to facilitate dispersion. For example, a useful wettable powder formulation contains 80.0 parts of the pesticidal compound, 17.9 parts of clay and 1.0 part of sodium lignosulfonate and 0.3 part of sulfonated aliphatic polyester as wetting agents. Additional wetting agent and/or oil will frequently be added to a tank mix to facilitate dispersion on the foliage of the plant.

Water-Dispersible Granules (WDG or DG) are dry compositions of the coated pesticide that will disperse in water yielding a dispersion of primary particles. Pesticide contents may range from 10-70% w/w. Polymers are used as dispersants (polyacrylate salts and lignosulfonate salts) and as binders to hold the granule together. Advantages of the dry product are that less potential for hydrolysis exists and high pesticide content may be achievable. Disadvantages are a more complex process involving milling blending extrusion and drying. Usually excipients are solids in this formulation.

Other useful formulations for the pesticidal compositions of the invention include suspo-emulsions, flowable formulations, and suspension concentrates.

Flowable formulations consist of particles of the coated pesticide suspended in a liquid carrier, generally water. Flowables, may include a small amount of a surfactant as a wetting agent and dispersants that are generally anionic or nonionic, and will typically contain pesticides in the range of 5% to 95%, frequently from 10 to 50%, by weight of the composition. For application, flowables may be diluted in water or other liquid vehicle, and are normally applied as a spray to the area to be treated.

Suspension concentrates (SC) are dispersions of finely particles (e.g. 2-15 micron) of coated pesticide in water. Pesticide contents range from 8-50% w/w. They are pourable, easily dispersible in water and should be stable to settling in the package. Polymers such as xanthan gum are used to prevent settling by increasing the yield stress of the suspension. Some polymeric dispersants, such as polyacrylic acid salts, are used. The dispersions may be stabilized against flocculation by use of polymers such as methacrylate grafted with polyethylene glycol (Atlox). Ethylene oxide/propylene oxide copolymers may be used to provide some stabilization after dilution.

Suspo-emulsions (SE) are dispersions of water immiscible liquids and fine particles (e.g. 2-15 micron) of coated pesticide in water. Pesticide contents range from 8-50% w/w. They are pourable, easily dispersible in water and should be stable to settling in the package. They contain several surfactants, in order to both stabilize the particles and emulsify the liquids. Some polymeric dispersants, such as polyacrylic acid salts, are used. SEs, like SCs, may be stabilized against flocculation by use of polymers such as methacrylate grafted with polyethylene glycol (Atlox). Ethylene oxide/propylene oxide copolymers may be used to provide some stabilization after dilution.

Useful formulations include suspensions of the coated pesticide in a relatively non-volatile solvent such as water, corn oil, kerosene, propylene glycol, or other suitable solvents. Granular formulations, wherein the coated pesticide is carried on relative coarse particles, are of particular utility for aerial distribution or for penetration of cover crop canopy. Pressurized sprays, typically aerosols wherein the coated pesticide is dispersed in finely divided form as a result of vaporization of a low-boiling dispersant solvent carrier may also be used. Water-dispersible granules are free flowing, non-dusty, and readily water-miscible. In use by the farmer on the field, the granular formulations, suspo-emulsions, flowable concentrates, aqueous emulsions, solutions, etc., may be diluted with water to give a concentration of pesticide in the range of e.g., 0.2-2%.

Method of Controlling Pests

In a further aspect, this invention is directed to a method of controlling pests comprising applying to the locus of such pests a pesticidally effective amount of the pesticidal compositions described herein. Such locus may be where pests are present or are likely to become present.

In applying the compositions of this invention, whether formulated alone or with other agricultural chemicals, an effective amount and concentration of the active compound is employed; the amount may vary in the range of, e.g. about 0.001 to about 3 kg/ha, or in some embodiments about 0.03 to about 2 kg/ha. For field use, where there are losses of pesticide, higher application rates (e.g., four times the rates mentioned above) may be employed.

The pesticidal compositions of this invention may be applied either as water-diluted sprays, or dusts, or granules to the areas in which suppression of pests is desired. These formulations may contain as little as 0.1% to as much as 35% or more by weight of pesticide. Dusts are free flowing admixtures of the pesticide compositions of the invention with finely divided solids such as talc, natural clays, kieselguhr, flours such as walnut shell and cottonseed flours, and other organic and inorganic solids which act as dispersants and carriers for the pesticide. These finely divided solids have an average particle size of less than about 50 microns. A typical dust formulation useful herein is one containing 1.0 part or less of the pesticidal composition and 99.0 parts of talc.

Different application methods are used for the pesticide formulations depending on the target pest, e.g., weed, fungus, or insect, and on the type of crop being treated. Application of pesticide may be by spraying for example solutions, emulsions or dispersions including coated pesticide to achieve accurate and even concentration over the entire treated area or target. Usually, the water used to dilute the pesticide composition in the spray mixture amounts to approximately 5-80 gallons per acre and the active ingredient amount may range approximately from 20 to 1000 grams per acre.

Pesticides may also be applied by broadcast spreading of granular formulations using machinery to achieve even distribution over the entire target. The coated pesticide may be incorporated into granular formulations by using a sticker (additional surfactant, polymer solution, or latex) to attach the pesticide to an inert support. Other granules are prepared by extrusion of powdered coated pesticide with inert powdered ingredients, water, binders, and dispersants to form granules that are subsequently dried. Pre-formed granular supports are often used to absorb liquid pesticide or solutions of the pesticide.

Formulations of these types are normally used to deliver pesticides to the soil before emergence of the crop. The target may be weed seeds or insects residing at different depths in the soil. There are two types of water used in the formulation and application of the compositions of the invention. The first is the water used to dilute the concentrates for application. The second type of water is the water that interacts with the coated pesticide after application. This water includes water from the environment such as rain water or water from irrigation systems. Movement of the pesticide through the soil is generally affected and controlled by rainfall. Generally, the pesticide composition is dissolved or dispersed in water originating from a spray solution or from a spray solution or from rainfall, after application.

EXAMPLES

In the examples below:

Unless otherwise indicated "%" refers to weight per weight (w/w) %.

"BPO (75%)" refers to 75% w/w BPO (Benzoyl peroxide) with 25% w/w water.

"Ludox TM 50 (50%)" refers to a dispersion of silica nanoparticles (average particle size diameter of about 20-30 nm) in water (50% w/w in water). Ludox TM 50 was obtained from Sigma-Aldrich, Israel.

"Ludox AM-30" refers to colloidal silica stabilized with sodium aluminate and dispersed in water (30% w/w in water). Ludox AM-30 was obtained from Sigma-Aldrich, Israel.

"CTAC (29%)" refers to a solution of cetyl trimethyl ammonium chloride 29% w/w in water.

"PVA (10%)" refers to a solution of polyvinyl alcohol 10% w/w in water.

"sodium silicate (25%)" refers to a solution of sodium silicate 25% w/w in water.

"GMIS" refers to glyceryl monoisostearate. GMIS was obtained from Scher Chemicals, USA.

"aluminum sulfate solution (50%)" or "aluminum sulfate (50%)" refers to a solution of aluminum sulfate decaoctahydrate 50% w/w in water.

"PDAC 7 (5%)" refers to a solution of polyquaternium 7 (Diallyldimethylammonium chloride/acrylamide copolymer), 5% w/w in water.

"CMC (10%)" refers to a solution of sodium salt of carboxymethyl cellulose 10% w/w in water.

"sodium aluminate (50%)" refers to solution of sodium aluminate 50 w/w in water.

"sodium borate (5%)" refers to solution of sodium borate 5% w/w in water.

"sodium alginate (5%)" refers to solution of sodium alginate 5% w/w in water.

"PPP K30 (40%)" refers to solution of PVP K30 (Polyvinylpyrrolidone K-30) 40% w/w in water.

Example 1

Encapsulation of BPO (Benzoyl Peroxide) (BPO Dispersed in DC-246)

a) Preparing the oil phase: A mixture of 67.68 g BPO (75%), 132.04 g DC-246 (cyclohexasiloxane, Dow Cornig, USA) and 10.06 g Span 65 as dispersant agent and 45.6 g of TEOS (tetraethoxy silane) were milled first by high shear at 4000 rpm for 2 minutes and then by microfluidizer for 15 minutes.

b) Preparing the water phase: An aqueous phase including 6.06 g of Myrj 45 (polyoxyethylene (8) stearate), 2.68 g CTAC (29%), 64.54 g PVA (10%) and 328.13 g of water was prepared.

The oil phase (a) was added to the water phase (b) under shearing at 6000 rpm for 2 minutes. Then, 49.93 g of Ludox TM 50 (50%) and 5 ml of sodium silicate (25%) were added, and then the pH was adjusted to 3. The mixture was transferred to reactor and stirred for 20 h.

Example 2

Encapsulation of BPO (BPO Dispersed in DC-350)

a) Preparing the oil phase: A mixture of 67.49 g BPO (75%), 130.92 g DC-350 (polydimethylsiloxane, obtained from Dow corning, USA) and 10.16 g cetyl alcohol as dispersant agent and 45.42 g of TEOS were milled first by high shear at 4000 rpm for 2 minutes and then by microfluidizer for 15 minutes.

b) Preparing the water phase: A water phase including 5.69 g of Myrj 45 (polyoxyethylene (8) stearate), 2.25 g CTAC (29%), 65.05 g PVA (10%) and 327.24 g of water, was prepared.

The two phases were preheated at 50° C. and then the oil phase (a) was added to the water phase (b) under shearing at 5000 rpm for 2 minutes. Then, 50.09 g of Ludox TM 50 (50%) were added and the solution became viscous. Then, 5 ml of sodium silicate (25%) was diluted up to 100.09 g with water and the resulted solution was added to the viscous mixture under shearing of 5000 rpm for 1 minute. The pH was adjusted to 3 and then the mixture was transferred to reactor and stirred for 20 h.

Example 3

Encapsulation of BPO (BPO Dispersed in Squalane)

a) Preparing the oil phase: A mixture of 68.64 g BPO (75%), 129.58 g squalane (obtained fron from Lake Oil, Spain) and 5.08 g GMIS as dispersant agent and 89.85 g of TEOS were milled first by high shear at 10000 rpm for 2 minutes and then by microfluidizer for 15 minutes.

b) Preparing the water phase: A water phase including 1.18 g CTAC (29%), 65.10 g PVA (10%) and 329.93 g of water, was prepared.

The oil phase (a) was added to the water phase (b) under shearing at 5000 rpm for 30 seconds. Then, 49.64 g of Ludox TM 50 (50%) was added and shearing continued further 30 seconds. Then, 20.72 g of aluminum sulfate solution (50%) were added and the obtained pH was 3. The mixture was transferred to reactor preheated at 40° C. and the mixture was stirred at 118 rpm for 4 hours. Then, the temperature was decreased to room temperature and stirring continued for 20 h.

Example 4

Encapsulation of BPO (BPO Dispersed in Squalane)

a) Preparing the oil phase: A mixture of 80.63 g BPO (75%), 108.15 g squalane (obtained from Lake Oil, Spain) and 5.71 g GMIS as dispersant agent and 27.97 g of TEOS were milled first by high shear at 10000 rpm for 1 minute and then by microfluidizer for 15 minutes.

b) Preparing the water phase: A water phase including 1.02 g CTAC (29%), 60.27 g PVA (10%) and 290.09 g of water, was prepared.

The oil phase (a) was added to the water phase (b) under shearing at 5000 rpm for 30 seconds. Then, 30.58 g of Ludox TM 50 (50%) was added and shearing continued further 30 seconds. Then, 20.09 g of aluminum sulfate solution (50%) were added under shearing for 30 seconds and the obtained pH was 3.2. The mixture was transferred to reactor preheated at 40° C. and the mixture was stirred at 100 rpm for 4 hours. Then, the temperature was decreased to room temperature and stirring continued for 20 h.

Example 5

Encapsulation of BPO (BPO Dispersed in Squalane)

a) Preparing the oil phase: A mixture of 53.19 g BPO (75%), 75.21 g squalane and 5.12 g GMIS as dispersant agent and 80.68 g of TEOS were milled first by high shear at 10000 rpm for 1 minute and then by microfluidizer for 15 minutes.

b) Preparing the water phase: A water phase including 4.16 g CTAC (29%), 6.5 g PVA (10%) and 280.45 g of water, was prepared.

The oil phase (a) was added to the water phase (b) under shearing at 5000 rpm for 30 seconds. Then, 90.11 g of Ludox TM 50 (50%) was added and shearing continued further 30 seconds. Then, 9.96 g of aluminum sulfate dissolved in 15.19 g water were added and the resulted mixture was milled at 6100 rpm for 1 minute. The mixture was then transferred to reactor preheated at 38.8° C. and it was stirred at 118 rpm for 4 hours. Then, the temperature was decreased to room temperature and stirring continued for 20 h.

Example 6

Encapsulation of BPO (BPO Dispersed in Squalane)

a) Preparing the oil phase: A mixture of 106.35 g BPO (75%), 88.09 g squalane and 4.91 g GMIS as dispersant agent and 41.05 g of TEOS were milled first by high shear at 10000 rpm for 1 minute. A thick mixture was obtained and it could not be milled by microfluidizer.
b) Preparing the water phase: A water phase including 1.31 g CTAC (29%), 6.3 g PVA (10%) and 283.1 g of water, was prepared.

The oil phase (a) was added to the water phase (b) under shearing at 5000 rpm for 30 seconds. Then, 60.66 g of Ludox TM 50 (50%) was added and shearing continued further 30 seconds. Then, 50.18 g of aluminum sulfate (50%) were added and the resulted mixture was milled at 6000 rpm for 1 minute. The mixture was then transferred to reactor preheated at 41.8° C. and it was stirred at 100 rpm for 4 hours. Then, the temperature was cooled down to room temperature and stirring continued for 20 h.

Example 7

Encapsulation of BPO (BPO Dispersed in Squalane)

a) Preparing the oil phase: A mixture of 106.24 g BPO (75%), 61.12 g squalane and 5.65 g cetyl alcohol as dispersant agent and 60.49 g of TEOS were milled first by high shear at 10000 rpm for 1.5 minutes. A thick mixture was obtained and it could not be milled by microfluidizer.
b) Preparing the water phase: A water phase including 1.09 g CTAC (29%), 61.52 g PVA (10%) and 269.45 g of water, was prepared.

The oil phase (a) was added to the water phase (b) under shearing at 5000 rpm for 30 seconds. Then, 59.87 g of Ludox TM 50 (50%) was added and shearing continued further 1 minute. Then, 21.87 g of aluminum sulfate (50%) were added and the resulted mixture was milled at 6000 rpm for 1 minute. The mixture was then transferred to reactor preheated at 40° C. and stirred for 4 hours. Then, the temperature was cooled down to room temperature and stirring continued for 20 h.

Example 8

Encapsulation of BPO (BPO Dispersed in Squalane)

a) Preparing the oil phase: A mixture of 105.28 g BPO (75%), 130.13 g squalane and 5.48 g Span 20 and 32.51 g of TEOS were milled first by high shear at 10000 rpm for 1 minute. A thick mixture was obtained and it could not be milled by microfluidizer.
b) Preparing the water phase: An aqueous phase including 4.31 g CTAC (29%), 6.5 g PVA (10%) and 279.8 g of water, was prepared.

The oil phase (a) was added to the water phase (b) under shearing at 4000 rpm and then 90.41 g of Ludox™ 50 (50%) was added and shearing continued 1 minute. Then, 20.88 g of aluminum sulfate (50%) were added and the resulted mixture was milled at 5000 rpm for 1 minute. The mixture was then transferred to reactor preheated at 39.2° C. and stirred at 103 rpm for 4 hours. Then, the temperature was cooled down to room temperature and stirring continued for 60 h.

Example 9

Encapsulation of BPO (BPO Dispersed in Squalane)

a) Preparing the oil phase: A mixture of 80.25 g BPO (75%), 107.04 g squalane and 5.01 g cetyl alcohol and 30.40 g of TEOS were milled first by high shear at 10000 rpm for 1 minute. A thick mixture was obtained and it could not be milled by microfluidizer.
b) Preparing the water phase: A water phase including 4.33 g CTAC (29%), 6.16 g PVA (10%) and 279.59 g of water, was prepared.

The oil phase (a) was added to the water phase (b) under shearing at 4000 rpm and then 59.43 g of Ludox TM 50 (50%) was added, and then the resulted mixture was homogenized at 8000 rpm for 1 minute since the mixture was very thick. Then, 49.45 g of aluminum sulfate (50%) were added and the resulted mixture was milled at 8000 rpm for 30 seconds. The mixture was then transferred to reactor preheated at 41.2° C. and stirred at 103 rpm for 4 hours. Then, the temperature was cooled down to room temperature and stirring continued for 20 h.

Example 10

Encapsulation of BPO (BPO Dispersed in Squalane)

a) Preparing the oil phase: A mixture of 80.2 g BPO (75%), 93.5 g squalane (obtained from Lake Oil, Spain) and 5.38 g Span 20 and 42.07 g of TEOS were milled first by high shear at 10000 rpm for 1 minute and then by microfluidizer for 15 minutes.
b) Preparing the water phase: A water phase including 4.05 g CTAC (29%), 61.51 g PVA (10%) and 257.74 g of water, was prepared.

The oil phase (a) was added to the water phase (b) under shearing at 4000 rpm and then 61.42 g of Ludox TM 50 (50%) was added and shearing at 5000 rpm continued for 1 minute. Then, 21.1 g of aluminum sulfate (50%) were added and the resulted mixture was milled at 5000 rpm for 1 minute. The mixture was then transferred to reactor preheated at 41.2° C. and stirred at 103 rpm for 4 hours. Then, the temperature was cooled down to room temperature and stirring continued for 20 h.

Examples 11-21 relate to encapsulation of active ingredients with modifications in the process. The procedures are suitable for any active ingredient which is a liquid, or which can be dissolved or dispersed in a hydrophobic liquid, or solids that can melt and become liquid at low temperatures (30-60° C.).

Example 11

Procedure 1 for Encapsulation of General AI (Active Ingredient)

A water phase containing 8.6 g of CTAC (29%) diluted with water up to 150 g, is milled by high shear at 6000 rpm and then 150 g of the oil phase [including an AI and a sol-gel precursor e.g., TEOS, TMOS] is added and milling is continued for 1 minute. Then, 50 g of Ludox TM 50 (50%) is added and the resulted mixture is milled for 1 minute by high shear at 8000 rpm. The pH of the mixture is adjusted to 5 by adding HCl (5 N) and then 50 g of PVA (10%) and 5 g of sodium silicate (25%) are added and then the pH of the mixture is adjusted to 4. The mixture is then stirred for 20 hours.

Example 12

Procedure 2 for Encapsulation of General AI

A water phase containing 8.6 g of CTAC (29%) diluted with water up to 150 g, is milled by high shear at 6000 rpm and then 150 g of the oil phase (including an AI and a sol-gel precursor e.g., TEOS, TMOS) is added and milling is continued for 1 minute. Then, 50 g of Ludox TM 50 (50%) is added and the resulted mixture is milled for 1 minute by high shear at 8000 rpm. The pH of the mixture is adjusted to 5 by adding HCl (5 N) and then 50 g of PVA (10%) and 5 g of sodium silicate (25%) are added and then the pH of the mixture is adjusted to 4. The mixture is then stirred for 20 hours. Then, 40 g of PDAC 7 (5%) is added till the zeta-potential is +20 my. After that, a solution of CMC (10%) (25 g) is added gradually till obtaining negative zeta-potential (of −20 my). During the additions the mixture was kept under milling of 7000 rpm.

Example 13

Procedure 3 for Encapsulation of General AI

A water phase containing 8.6 g of CTAC (29%) diluted with water up to 150 g, is milled by high shear at 6000 rpm and then 150 g of the oil phase (including an AI and a sol-gel precursor e.g., TEOS, TMOS) is directly added and milling is continued for 1 minute. Then, 50 g of Ludox TM 50 (50%) is added and the resulted mixture is milled for 1 minute by high shear at 8000 rpm. The pH of the mixture is adjusted to 5 by adding HCl (5 N) and then 50 g of PVA (10%) and 10 g of sodium aluminate (50%) are added and then the pH of the mixture is adjusted to 4. The mixture is then stirred for 20 hours.

Example 14

Procedure 4 for Encapsulation of General AI

A water phase containing 8.6 g of CTAC (29%) diluted with water up to 150 g, is milled by high shear at 6000 rpm and then 150 g of the oil phase (including an AI and a sol-gel precursor e.g., TEOS, TMOS) is added and milling is continued for 1 minute. Then, 50 g of Ludox™ 50 (50%) is added and the resulted mixture is milled for 1 minute by high shear at 8000 rpm. The pH of the mixture is adjusted to 5 by adding HCl (5 N) and then 50 g of PVA (10%) and 50 g of sodium borate (5%) are added and then the pH of the mixture is adjusted to 4. The mixture is then stirred for 20 hours.

Example 15

Procedure 5 for Encapsulation of General AI

A water phase containing 8.6 g of CTAC (29%) diluted with water up to 150 g, is milled by high shear at 6000 rpm and then 130 g of the oil phase (including an AI) and 20 g of dimethyl dimethoxysilane are added and milling is continued for 1 minute. Then, 50 g of Ludox TM 50 (50%) is added and the resulted mixture is milled for 1 minute by high shear at 8000 rpm. The pH of the mixture is adjusted to 3 by adding HCl (5 N) and the mixture is then stirred for 20 hours.

Example 16

Procedure 6 for Encapsulation of General AI

A water phase containing 8.6 g of CTAC (29%) diluted with water up to 150 g, is milled by high shear at 6000 rpm and then 130 g of the oil phase (including an AI) and 20 g of dimethyl dimethoxysilane are added and milling is continued for 1 minute. Then, 50 g of Ludox™ 50 (50%) is added and the resulted mixture is milled for 1 minute by high shear at 8000 rpm. Then, 25 g of aluminum sulfate (50%) and 50 g of PVA (10%) are added and the resulted mixture is stirred for 24 hours.

Example 17

Procedure 7 for Encapsulation of General AI

A water phase containing 8.6 g of CTAC (29%) diluted with water up to 150 g, is milled by high shear at 6000 rpm and then 130 g of the oil phase (including an AI) and 20 g of Al(O$^i$Pr)$_3$ ($^i$Pr stands for isopropyl) are added and milling is continued for 1 minute. Then, 50 g of Ludox™ 50 (50%) is added and the resulted mixture is milled for 1 minute by high shear at 8000 rpm. The pH of the mixture is adjusted to 3 by adding HCl (5 N) and the mixture is then stirred for 20 hours.

Example 18

Procedure 8 for Encapsulation of General AI

A water phase containing 8.6 g of CTAC (29%) diluted with water up to 150 g, is milled by high shear at 6000 rpm and then 130 g of the oil phase (including an AI) and 20 g of Ti(O$^i$Pr)$_4$ ($^i$Pr=isopropyl) are added and milling is continued for 1 minute. Then, 50 g of Ludox TM 50 (50%) is added and the resulted mixture is milled for 1 minute by high shear at 8000 rpm. The pH of the mixture is adjusted to 3 by adding HCl (5 N) and the mixture is then stirred for 20 hours.

Example 19

Procedure 9 for Encapsulation of General AI

A water phase containing 8.6 g of CTAC (29%) diluted with water up to 150 g, is milled by high shear at 6000 rpm and then 130 g of the oil phase (including an AI), 20 g of TEOS and 5 g of dimethyl dimethoxysilane are added and milling is continued for 1 minute. Then, 50 g of Ludox TM 50 (50%) is added and the resulted mixture is milled for 1 minute by high shear at 8000 rpm. The pH of the mixture is adjusted to 3 by adding HCl (5 N) and the mixture is then stirred for 20 hours.

Example 20

Procedure 10 for Encapsulation of General AI

A water phase containing 8.6 g of CTAC (29%) diluted with water up to 150 g, is milled by high shear at 6000 rpm and then 130 g of the oil phase (including an AI) and 20 g of TEOS are added under milling for 1 minute at 6000 rpm. Then, 50 g of Ludox TM 50 (50%) is added and the resulted mixture is milled for 1 minute by high shear at 8000 rpm. The pH of the mixture is adjusted to 5 by adding HCl (5 N) and then 50 g of PVA (10%) and 10 g of calcium chloride are added and then the pH of the mixture is adjusted to 4. The mixture is then stirred for 20 hours.

Example 21

Procedure 11 for Encapsulation of General AI

A water phase containing 8.6 g of CTAC (29%) diluted with water up to 150 g, is milled by high shear at 6000 rpm and then 150 g of the oil phase (including an AI and a sol-gel precursor e.g., TEOS, TMOS)) is added and milling is continued for 1 minute. Then, 50 g of Ludox TM 50 (50%) is added and the resulted mixture is milled for 1 minute by high shear at 8000 rpm. The pH of the mixture is adjusted to 5 by adding HCl (5 N). Then, 40 g of PDAC 7 (5%) is added till the zeta-potential is +20 mv. After that, a solution of sodium alginate (5%) (35 g) is added gradually till obtaining negative zeta-potential (of −20 mv). During the additions the mixture was kept under milling of 7000 rpm. Then, 5 g of calcium chloride is added and the resulted mixture is stirred for 2 hours.

Examples 22-24 relate to oil-dispersed encapsulation of ATRA (all-trans retinoic acid).

Example 22

Encapsulation Using an Oil Phase Comprising Squalane Oil and Tretinoin a) Preparing the oil phase: 10 g of Tretinoin 4 g of BHT (butyl hydroxytoluene) (40% of Tretinoin weight), 100 g of squalane oil, and 2 g of GMIS were mixed under stirring at room temperature. Then the mixture was milled by high shear homogenizer at 12000 rpm for 2 min to obtain particle size of about 30 micron. The resulted suspension was milled in a microfluidizer for 30 min to obtain particles of 3-7 micron in size. 49.7 g of TEOS (TEOS/oil weight ratio 30/70 was added to the suspension under stirring.

b) Preparing the water phase: 285.5 g of TDW (tridistilled water), 1 g of CTAC (cetyl trimethyl ammonium chloride) (29%) w/w in water and 100 g of 10% PVA were mixed under stirring. Oil phase/water phase (OP/WP) weight ratio was 30/70.

Emulsion was prepared at 4000 rpm for 1 min. Immediately after emulsification 20 g of Ludox AM-30 was added at 3500 rpm, mixing time 30 sec. Then 30 g of aluminum sulfate was added at 3000 rpm, mixing time 2 min. The reaction mixture was kept at 40° C. for 4 hr (aging) under stirring.

Optionally the capsules were coated with polymers as follows. To the emulsion 110 g of 5% PDAC-7 was added at 3500-4000 rpm, Z potential was +3 mV. Then 120 g of 5% CMC was added at 3500-4000 rpm, −Z potential was −2 mV.

Coating of capsules with polymers strengthens the capsules and should be, in some embodiment, be made within Z potential limits from +3 mV to +5 mV for PDAC-7 and within Z potential limits from −3 mV to −5 mV for CMC.

Example 23

Encapsulation Using an Oil Phase Comprising Castor Oil and Tretinoin a) Preparing the oil phase: 10 g of Tretinoin, 4 g of BHT, 100 g of castor oil) and 2 g of GMIS were mixed and stirred at 40° C. 49.7 g of TEOS was added (TEOS/oil weight ratio 30/70) Then the mixture was milled by high shear homogenizer at 12000 rpm for 2 min to obtain particle size of about 30 micron. The resulted suspension was milled in a microfluidizer for 30 min.

b) Preparing the water phase: 285.6 g of tridistilled water, 1 g of CTAC (29%) and 40 g of PVA (10%) were mixed under stirring and heated to 40° C. Oil phase/water phase (OP/WP) weight ratio was 30/70.

Emulsion was prepared at 5000 rpm for 1 min. Immediately after emulsification 60 g of Ludox AM-30 was added at 3500-4000 rpm. Then, 150 g of aluminum sulfate solution (50%) was added. The reaction mixture was kept at 40° C. for 4 hr under stirring.

Optionally the capsules were coated with polymers as follows. To the emulsion 105 g of 5% PDAC-7 was added at 4000 rpm, Z potential was +3.5 mV. Then 275 g of 10% CMC was added at 4000 rpm, Z potential was −−1.5 mV.

Coating of capsules with polymers should be within Z potential limits from +3 mV to +5 mV for PDAC-7 and within Z potential limits from −3 mV to −5 mV for CMC.

Example 24

Encapsulation Using an Oil Phase Comprising Cyclomethicone DC-246 Oil and Tretinoin Tretinoin crystals dispersed in DC-246 were milled in Dyno-mill MutiLab KD 0.3 L for 10 min at 27° C. Tretinoin particles were obtained with d(0.9)<3 micron, (which were smaller than those milled in microfluidizer), and thus facilitated inclusion of Tretinoin crystals into emulsion drops. Milling proceeded successfully without dispersant addition.

Oil phase preparation: 50 g of TEOS was added to 114 g of the milled material containing 10 g of Tretinoin, 4 g of BHT and 100 g of DC-246, the mixture was stirred.

Water phase preparation: 285.6 g of tridistilled water, 5 g of CTAC (29%) and 80 g of PVA were mixed.

Emulsion was prepared by addition of oil phase to water phase at 5000 rpm for 1 min. Immediately after emulsification 50 g of Ludox AM-30 was added at 4000 rpm, mixing time was 1 min. Then 47 g of aluminum sulfate solution (50%) was added at 4000 rpm, mixing time was 1 min.

To the emulsion 85 g of PDAC-7 (5%) was added at 4000 rpm, Z potential was +5.8 mV. Then 254 g of CMC (10%) was added at 4000 rpm, Z potential was −4.5 mV.

Coating of capsules with polymers should be within Z potential limits from +3 mV to +5 mV for PDAC-7 and within Z potential limits from −3 mV to −5 mV for CMC.

Example 25

Encapsulation of Carbosulfan 75 g Water (deionized) and 25 g Agrimer AL-10LC (1-butene vinyl pyrrolidone polymer, International Specialty Products (ISP), USA) 5% solution in water, were charged to a 1000-mL Blender (Waring, variable speed). 70 g Carbosulfan (88.8%, FMC, USA) homogeneously mixed with 6 g tetramethoxysilane (Aldrich, USA) in a separate vessel was charged. The two phases were combined and the mixture was blended at 9000 RPM for 2 min. 20 g Ludox TM-50 (colloidal silica suspension, 50% in water, Aldrich, USA) was added and homogenized 40 sec at 8000 RPM. 30 g Ludox TMA (colloidal silica suspension, 34% in water, Aldrich, USA) was added and further homogenized 40 sec at 8000 RPM. The particle size was determined using a Horiba LA910 particle size analyzer (D90<10 μm).

The dispersion was poured to a jacketed reaction vessel equipped with a paddle-type Teflon stirrer blade, and stirred gently at room temperature. The pH was adjusted to pH 3.0 using 6 N HCl. The reaction vessel was purged with a gentle stream of nitrogen to remove formed MeOH, and stirring was continued for 24 hr. Suspension pH was adjusted to 7.5 by addition of saturated NaHCO3 (ca. 5 g). Suspension (21.3 wt. % assay) was bottled and stored.

Example 26

Encapsulation of Metolachlor with TMOS 90 g 5% Na2SO4 solution (J. T. Baiker, USA) and 22 g Agrimer DA 102W (~2% solution in water, ISP (International Specialty Products, ISP, USA)) were charged to a 1000-mL Blender (Waring, variable speed). 52.0 g Metolachlor 98.8%, (Agan Chemical Manufacturers, Israel) homogeneously mixed with 6.0 g aromatic 200 (ExxonMobile-USA), 5.2 g tetramethoxysilane (Aldrich, USA) and 1.0 g epoxidized soyabean oil in a separate vessel was charged. The two phases were combined and the mixture was blended at 9000 RPM for 2 min. 20 g Ludox TM-50 (colloidal silica suspension, 50% in water, Aldrich, USA) was added and homogenized 40 sec at 9000 RPM. 20 g Ludox TMA (colloidal silica suspension, 34% in water, Aldrich, USA) was added and further homogenized 40 sec at 8000 RPM. The particle size diameter was determined using a Horiba LA910 particle size analyzer (D90<10 μm).

The dispersion was poured to a jacketed reaction vessel equipped with a paddle-type Teflon stirrer blade, and stirred gently at room temperature. The pH was adjusted to pH 2.0 using 6 N HCl. The reaction vessel was purged with a gentle stream of nitrogen to remove formed MeOH, and stirring was continued for 24 hr. Suspension pH was adjusted to 4.1 by addition of saturated NaHCO3 (ca. 1 g). 40 g of water and 10 g PVP K30 (40%) was added, and the mixture was sheared at 3500 RPM for 3 min. The encapsulated metolachlor with 22 wt. % assay was bottled.

Example 27

Encapsulation of Clomazone 150 ml water (deionized) was mixed with 25 g Agrimer-10LC (5% aqueous solution) in a stainless steel beaker. 20 g Ludox TM 50 (50%) was added while mixing. The solution was neutralized to pH 7 using 1 N HCl.

In a separate bottle, 120 g clomazone (91% assay) was mixed with 30 g tetramethoxysilane (99% purity, TMOS) until a homogeneous solution was obtained.

While mixing the aqueous solution using a Silverson L4R homogenizer the clomazone/TMOS solution was added and the mixture homogenized at 5000 rpm for 1 minute. The resulting emulsion was transferred to a jacketed resin flask equipped with a propeller stirrer and 2 g aluminum sulfate ($Al_2(SO_4)_3$ 18 hydrate in 50 ml $H_2O$) was added in portions to the stirring slurry.

Sample was stirred at 250 rpm overnight at 30° C.

While this invention has been shown and described with reference to preferred embodiments thereof, it will be understood by those skilled in the art that many alternatives, modifications and variations may be made thereto without departing from the spirit and scope of the invention. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

The invention claimed is:

1. A process of preparing microcapsules comprising a core material encapsulated by a metal oxide shell, said process comprising:
    (a) preparing an oil-in-water emulsion by emulsification of an oily phase that comprises a core material, in an aqueous phase, wherein one or both of the oily phase and the aqueous phase comprise a sol-gel precursor;
    (b) adding metal oxide nanoparticles to said aqueous phase prior to the preparation of the emulsion of step (a), or adding the metal oxide nanoparticles during the preparation of the emulsion of step (a) or adding the metal oxide nanoparticles after the preparation of the emulsion of step (a); and
    (c) applying conditions to obtain microcapsules;
        wherein said core material comprises a pharmaceutically, cosmetically, or agrochemically active ingredient, wherein the active ingredient is in a solid form and dispersed in the core, and wherein said metal oxide is selected from silica, titania, zirconia, ZnO, and mixtures thereof.

2. The process of claim 1, wherein said core material comprises a dermatologically active agent, selected from antifungal agents, antibacterial agents, anti-inflammatory agents, antipruritic agents, anti psoriatic agent, anti acne agents, anti rosacea agents, and combinations of any of the above.

3. The process of claim 1, wherein said core material comprises an anti acne agent selected from benzoyl peroxide, retinoid, and mixtures thereof.

4. The process of claim 1, wherein said core material comprises an agrochemically active ingredient which is a pesticide.

5. The process of claim 1, further comprising adding a salt of a metal oxide .to said aqueous phase either prior, during or after step (a), wherein said salt of the metal oxide is selected from sodium silicate, potassium silicate, sodium titanate, potassium titanate, sodium zirconate, potassiunn zirconate, and mixtures thereof.

6. The process of claim 1, further comprising adding a binding or crosslinking additive to said aqueous phase either prior, during or after step (a) wherein said binding or cross-linking additive is selected from a polymeric agent, a di- or trivalent metal salt, a polyelectrolyte, and mixture thereof.

7. The process of claim 1, wherein the pH of said aqueous phase is in the range of 2-9.

8. The process of claim 1, said conditions comprise isolating the microcapsules through procedures selected from at least one of: separation by centrifuge, filtration, evaporation, re-suspension in aqueous medium, and dialysis.

9. The process of claim 1, wherein the product obtained is a suspension of said microcapsules.

10. The process of claim 1, wherein the product obtained is a powder of said microcapsules.

11. The process of claim 1, wherein in step (b) the metal oxide nanoparticles are added to said aqueous phase prior to the preparation of the emulsion of step (a).

12. The process of claim 1, wherein in step (b) the metal oxide nanoparticles are added after the preparation of the emulsion of step (a).

13. The process of claim 1, wherein in step (b) the metal oxide nanoparticles are added during the preparation of the emulsion of step (a).

* * * * *